United States Patent
Perkins et al.

(10) Patent No.: US 7,751,375 B2
(45) Date of Patent: Jul. 6, 2010

(54) COMMUNICATIONS SYSTEM AND PROTOCOL FOR MEDICAL ENVIRONMENT

(75) Inventors: Michael C. Perkins, Havana, IL (US); Lawrence W. Gallagher, Palatine, IL (US); Reuben P. Garcia, Evanston, IL (US)

(73) Assignee: Rauland-Borg Corporation, Mount Prospect, IL (US)

( * ) Notice: Subject to any disclaimer, the term of this patent is extended or adjusted under 35 U.S.C. 154(b) by 543 days.

(21) Appl. No.: 11/678,011

(22) Filed: Feb. 22, 2007

(65) Prior Publication Data
US 2008/0205310 A1 Aug. 28, 2008

(51) Int. Cl.
*H04J 3/00* (2006.01)
(52) U.S. Cl. .................. 370/336; 370/310; 370/330; 370/345
(58) Field of Classification Search .......... 370/229, 370/235, 236, 241, 242, 252, 310, 328, 329, 370/330, 336, 343, 345, 431, 436, 437; 439/557, 439/625, 626, 660, 950
See application file for complete search history.

(56) References Cited

U.S. PATENT DOCUMENTS

| | | | |
|---|---|---|---|
| 4,934,468 | A | 6/1990 | Koerber, Sr. et al. |
| 6,092,102 | A | 7/2000 | Wagner |
| 6,445,299 | B1 | 9/2002 | Rojas |
| 6,693,514 | B2 | 2/2004 | Perea, Jr. et al. |
| 6,791,460 | B2 | 9/2004 | Dixon et al. |
| 6,822,571 | B2 | 11/2004 | Conway |
| 7,508,307 | B2 | 3/2009 | Albert |
| 7,538,659 | B2 | 5/2009 | Ulrich et al. |
| 2002/0014951 | A1 | 2/2002 | Kramer et al. |
| 2005/0035871 | A1 | 2/2005 | Dixon et al. |
| 2007/0004971 | A1 | 1/2007 | Riley et al. |
| 2007/0010719 | A1* | 1/2007 | Huster et al. ................ 600/300 |

(Continued)

FOREIGN PATENT DOCUMENTS

WO  PCT/US2007/062610  2/2007

OTHER PUBLICATIONS

U.S. Appl. No. 11/678,035, filed Feb. 22, 2007, Perkins et al.

(Continued)

*Primary Examiner*—Chi H Pham
*Assistant Examiner*—Weibin Huang
(74) *Attorney, Agent, or Firm*—Leydig, Voit & Mayer, Ltd.

(57) ABSTRACT

A communications system and protocol are described for wirelessly interconnecting a pair of bed and wall units that communicate the patient information, including bed exit alerts, from the patient supporting equipment to the hospital nurse call system. A linking procedure is provided for establishing a communications link to interconnect the pair of units, wherein the communications link fails upon detection of a third communications device simultaneously undergoing the link attempt mode. In one embodiment, the system provides for advanced collision detection by monitoring corruption of the end-of-packet byte within the periodic check-in message sequences between the linked units to prevent data corruption and future collisions. To ensure prompt interconnection of units, embodiments of the invention provide for a link reminder to alert the health care provider to initiate the steps for linking the bed and wall units whenever two or more unlinked units are in proximity.

36 Claims, 13 Drawing Sheets

U.S. PATENT DOCUMENTS

| | | | |
|---|---|---|---|
| 2007/0054641 | A1 | 3/2007 | Goedicke et al. |
| 2007/0110097 | A1* | 5/2007 | Hsieh ........................ 370/464 |
| 2007/0183360 | A1* | 8/2007 | Arunan et al. .............. 370/328 |

OTHER PUBLICATIONS

U.S. Appl. No. 11/678,042, filed Feb. 22, 2007, Perkins et al.

PowerPoint presentation entitled "WPAN", Teknillinen Korkeakoulu, 44 pages, accessed at www.comlab.hut.fi/studies/3240/luentokalvot/2_wpan.ppt on Jan. 22, 2007 (no specified date but no later than applicants' filing date).

PowerPoint presentation entitled "Introduction", Teknillinen Korkeakoulu, 29 pages, accessed at www.comlab.hut.fi/studies/3240/luentokalvot/1introduction.ppt on Jan. 23, 2007 (no specified date but no later than applicants' filing date).

Product brochure entitled "I need to care for more patients than ever, in less time, and keep them safe. How Do I Do that?", Stryker, Copyright 2007 USA, 4 pages, accessed at www.med.stryker.com/product.jsp?id-18dcid=1 on Feb. 5, 2007.

Product brochure entitled "GoBed II® Med/Surg Bed", Stryker, Copyright 2005, 2 pages, accessed at www.med.stryker.com/product.jsp?id-1acid=1 on Feb. 5, 2007.

Product brochure entitled "Bed Awareness™ Option", Stryker, Copyright 2007, 1 page, accessed at www.med.stryker.com/product.jsp?id-18acid=1 on Feb. 5, 2007.

Product brochure entitled "Responder® Net", Rauland-Borg Corporation, 2 pages, accessed at http://www.rauland.com/healthcare/resnet_network.htm on Feb. 7, 2007 (no specified date but no later than applicants' filing date).

Product data sheet entitled "XE1203F", SEMTECH Corporation, Rev Aug. 1, 2005, 36 pages, accessed at www.semtech.com on Feb. 8, 2007.

Product data sheet entitled "PSoC® Mixed-Signal Array Final Data Sheet", Cypress Semiconductor Corp., Oct. 26, 2006, 51 pages, accessed at http://www.cypress.com on Feb. 8, 2007.

Product brochure entitled "Wireless Bed Interface: Improving Patient Safety and Reducing Maintenance", Rauland-Borg Corporation, 2 pages, accessed at www.Sagatechs.com/ODF_files/Wireless_Bed_Interface_Brochure.pdf on Feb. 22, 2007 (no specified date but no later than applicants' filing date).

Press Release entitled "First Wireless Bed Interface Launched at University of Wisconsin Hospitals & Clinics", Rauland-Borg Corporation, Jan. 3, 2007, 1 page, accessed at www.rauland.com/corporate/pdfs/prhc_Wireless_Bed_Interface.pdf on Feb. 22, 2007.

Newsletter entitled "Announcing the Availability of the New Wireless Bed Interface!", Rauland-Borg Corporation, Copyright 2007, 2 pages.

Article entitled "Improving Patient Safety and Reducing Maintenance Issues: Responder's Wireless Bed Interface", Rauland-Borg Corporation, 2 pages, (no specified date but no later than applicants' filing date).

International Search Report and Written Opinion for PCT/US2007/062610 mailed Feb. 26, 2008.

Product brochure entitled "Responder® Net", Rauland-Borg Corporation, (May 2003), 2 pages, accessed at http://www.rauland.com/healthcare/resnet_network.htm on Feb. 7, 2007.

Product brochure entitled "Wireless Bed Interface: Improving Patient Safety and Reducing Maintenance", Rauland-Borg Corporation, (Jan. 4, 2007), 2 pages, accessed at www.Sagatechs.com/ODF_files/Wireless_Bed_Interface_Brochure.pdf on Feb. 22, 2007.

Newsletter entitled "Announcing the Availability of the New Wireless Bed Interface!", Rauland-Borg Corporation, (Jan. 4, 2007), 2 pages.

Article entitled "Improving Patient Safety and Reducing Maintenance Issues: Responder's Wireless Bed Interface", Rauland-Borg Corporation, (Jan. 4, 2007), 2 pages.

USPTO, Office Action in related U.S. Appl. No. 11/678,042 mailed Sep. 8, 2009.

USPTO, Office Action in related U.S. Appl. No. 11/678,035 mailed Nov. 19, 2009.

Reply to Office Action, mailed by USPTO on Sep. 8, 2009 in related U.S. Appl. No. 11/678,042, filed Dec. 8, 2009.

* cited by examiner

COMMUNICATIONS SYSTEM AND PROTOCOL FOR MEDICAL ENVIRONMENT

CROSS REFERENCE TO RELATED APPLICATIONS

This application is related to U.S. application Ser. No. 11/678,035 to Perkins, Garcia, and Gallagher and U.S. application Ser. No. 11/678,042 to Perkins, Parrish, and Garcia, both entitled "Communications System And Protocol For Medical Environment" and both filed on Feb. 22, 2007. Each of above applications is incorporated by reference in its entirety herein.

FIELD OF THE INVENTION

This invention relates generally to the field of communications and more specifically to the field of medical communications devices.

BACKGROUND OF THE INVENTION

Modern health care environments place heavy burdens on medical personnel responsible for a continuously growing number of patients. Nursing shortages and heavy workloads continue to be the norm in most modern hospitals. Nursing and other front line medical caregivers are typically responsible for monitoring and reporting patient conditions. A patient's post-operative recovery, for example, often requires monitoring and restricting patient movement. This task is frequently complicated when dealing with patients who are confused or unable to understand the caregiver's instructions and are at risk of injury due to their propensity for excessive movement.

Patient movement and bed position detection systems provide monitoring and alerting capabilities by conveying to care giving personnel a patient's movement and/or position on the bed. These systems provide for remote monitoring and alerting by employing sensors incorporated into hospital beds or other patient supporting equipment that interface with a nurse call system to relay the sensor data to a nursing station or a telemetry unit. When the system detects that a patient has left the bed, changed positions and/or moved the bed controls in a way that does not comply with an allowed range of motion, nursing personnel are alerted to take appropriate action. Typically, patient movement and position sensors mounted in the bed interface with a control unit located on the bed. The control unit transmits the patient data to the nursing station via a cable that connects the control unit and a nurse call system interface located in the patient's room.

Patient beds and other patient equipment are often moved about a hospital. Upon moving the bed to another location, the cable connecting the bed to the nurse call system is disconnected for transport of the bed and then reconnected when the bed is prepared at its new location. Because the cable is a physical tether, it is easy for hospital personnel to forget to disconnect the cable before moving the bed or any other equipment cabled to the wall, causing damage to the cables and to the connectors on the bed and the wall Additionally, when the bed is being prepared at a new location, hospital personnel do not have the physical reminder to connect the cable.

BRIEF SUMMARY OF THE INVENTION

A wireless communications link and associated protocol interconnect a pair of bed and wall units that communicate patient information, including bed exit alerts, from a patient supporting equipment to a hospital nurse call system. In one embodiment, the bed/wall unit pair operates within unlicensed spectrum and, therefore, takes into account possibility of congestion and interference in order to provide safe and reliable connection to the nurse call system. Specifically, a linking procedure aids the establishment of a communications link between the bed and wall units and prevents unintended cross linking of the paired units to other nearby bed and wall units. During the linking procedure, the establishment of the communications link fails upon detection of a third communications device such as a bed or wall unit attempting to participate in the linking process.

Once established, the communications link is maintained by periodically exchanging link status or check-in message sequences between the linked bed/wall pair. The processing of the messages includes detecting collisions with link status messages generated by other linked bed/wall pairs. Early detection of collisions or interference among links is achieved by monitoring corruption of an end-of-packet or tail-feather byte within the periodic messages. As link status messages from different links slowly drift toward one another, the end-of-packet byte in one of the two messages will corrupt first. By responding to corruption of the end-of-packet byte, the data in the packet is saved so that the integrity of the link status message remains intact. Early detection of the collision enables the message to be adjusted either in time or frequency to avoid corruption of the links' integrity.

In one embodiment, the periodic link messages are time shifted upon detection of a collision of link status messages, which moves the messages away from the colliding messages that are also periodic. Although the interfering messages may share the same or a similar repetition period, by shifting the timing of one of the messages, the messages of one link no longer overlap messages of the other link detected by the collision. Other features include monitoring for combinations of first-try check-in message failure and first-resend success, as strong indications of colliding units, and adjusting the nominal time slot of periodic check-in messages. Alternatively, the linked bed/wall unit pair shifts to another operating channel upon detection of link status message collisions. To prevent interference from other devices sharing the same spectrum, the system also provides for monitoring channel noise and moving to a different operating channel to evade other interfering devices.

Preferably, the bed unit includes a local power source such as a battery. To ensure long lasting operation, the bed unit enters an idle sleep mode by temporarily powering down its transceiver circuitry.

To ensure prompt interconnection of units, embodiments of the invention provide for a link reminder to alert the health care provider to initiate the steps for linking the bed and wall units whenever two or more unlinked units are in proximity. The system broadcasts link reminder messages to elicit reply messages from one or more nearby unlinked units and activates a link reminder alert upon receipt of multiple replies from the same unlinked unit. When the system operates on multiple frequencies, unlinked units transmit link reminder messages on each of the system channels.

BRIEF DESCRIPTION OF THE SEVERAL VIEWS OF THE DRAWING(S)

While the appended claims set forth the features of the present invention with particularity, the invention and its advantages are best understood from the following detailed description taken in conjunction with the accompanying drawings, of which:

DETAILED DESCRIPTION OF THE INVENTION

Figure 1:
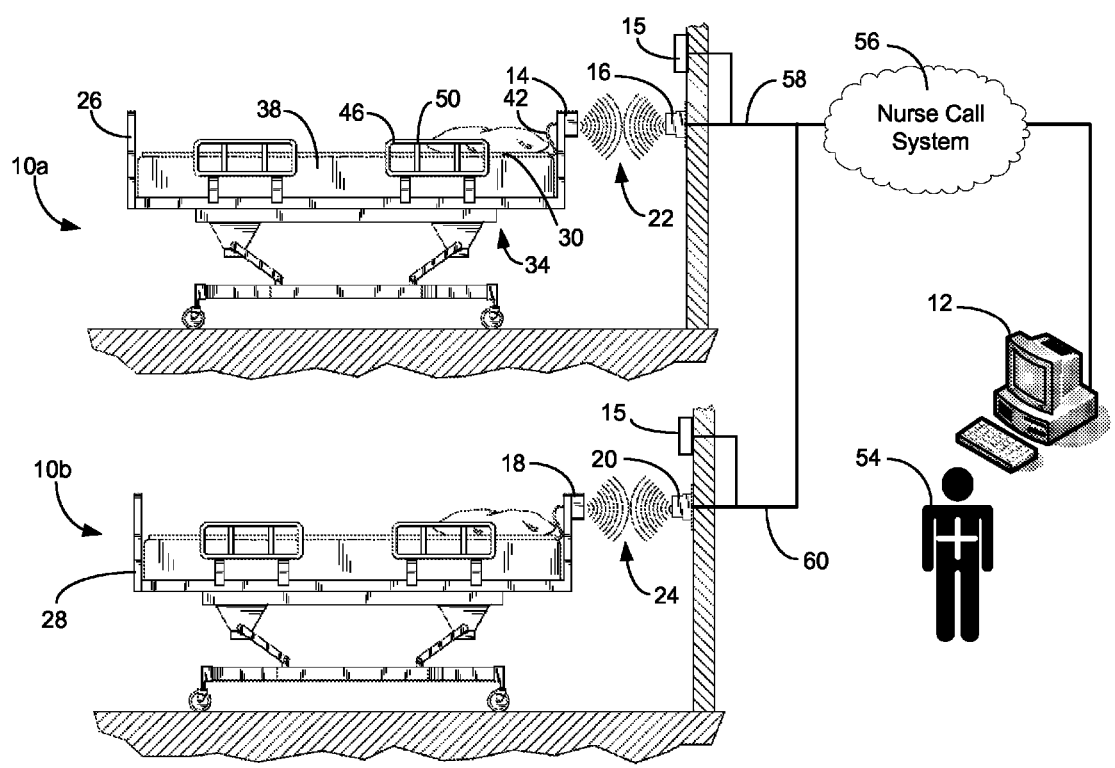
FIG. 1 is a schematic diagram illustrating a hospital facility environment having multiple hospital beds each wirelessly connected to a hospital monitoring and alerting system via a pairs of bed and wall units.

Turning to the drawings and referring first to FIG. 1, a typical hospital facility environment has multiple hospital beds connected to a hospital monitoring and alerting system. In FIG. 1, only two hospital rooms 10a and 10b are illustrated. Each of the rooms 10a and 10b are identically equipped.

For ease of explanation, whenever detailed reference is made hereinafter to the equipment in one of the rooms 10a and 10b, the description applies equally well to the other room in FIG. 1, unless indicated otherwise. Moreover, FIG. 1 is representative of a larger environment such as a hospital that may include many more rooms such as the two illustrated in FIG. 1 that are also equipped in the same or similar manner. All of the rooms may be connected to a common nurse call system as suggested by FIG. 1 or there may be several nurse call systems with each of them connecting a group of rooms. All such networking architectures and others are contemplated by the detailed description set forth herein.

To communicate patient information from the hospital room 10a to a monitor 12 at a remote nursing station, a bed and wall unit pair 14 and 16, respectively, is associated with a mobile hospital bed 26 through a wireless communications link 22. Preferably, the communications link 22 operates within an unlicensed frequency band, such as Industrial, Scientific, and Medical (ISM) frequencies allocated by the United States Federal Communications Commission (FCC) to be employed for low-power/short-range wireless communications. To reduce the chance of interference from other devices sharing the ISM frequencies, the communications link 22 preferably operates within the 902-928 MHz ISM frequency band and complies with the corresponding maximum transmit power limitations designated by the FCC for devices operating within this frequency range. Other contemplated frequency bands include other available ISM frequency bands, such as 2.4 GHz and 5.8 GHz bands. In the illustrated embodiment, the bed unit 14 is attached to the mobile hospital bed 26 for collecting the patient information, which includes patient occupancy, nurse call, call assurance, and system status signaling.

To convey the nurse call and call assurance signaling, the bed unit 14 interfaces with the patient communications module 46, which is located within the siderail 50. To communicate with the health care provider 54, a patient initiates a nurse call via the communications module 46. Once the patient places a nurse call, the communications module 46 generates a call assurance signal by activating a visual indicator (not shown), such as a status LED, to indicate that a nurse call has been placed. Similarly, when the maintenance of the communications link 22 is in jeopardy due to low battery power at the bed unit 14, or when the communications link 22 is lost, such as due to poor signal conditions or movement of the bed 26, the bed unit 14 or the wall unit 16 generates a "bed out" signal reflecting the system status.

Furthermore, to collect the patient occupancy information, a bed sensor 30 measures the interaction of the patient's body with the bed frame 34 and conveys the collected information to the bed unit 14 via a cable 42. Alternatively, there may be a wireless connection between the bed unit 14 and the bed sensor 30. An example of a bed sensor equipped hospital bed is a Chaperone® center of gravity bed exit system manufactured by Stryker Corporation located at 2825 Airview Boulevard, Kalamazoo, Mich. 49002. A typical bed exit system includes one or more occupancy sensors 30 distributed along a bed frame 34 to collect and analyze the weight information and determine the patient's occupancy status, such as whether the patient has left the bed 26 and/or the patient's position on the bed 26. In the illustrated embodiment, the bed sensor 30 is a pad type sensor placed on top of the mattress 38, while other embodiments include load cell sensors incorporated into the bed frame 34. The patient occupancy information generated by the bed exit system also includes a bed exit alarm signal generated by the occupancy sensor 30 when the patient moves off the bed frame 34. The patient occupancy information further includes patient weight, bedrail height, bed height, brake status, and bed support elevation angle.

Upon collecting the patient information, the bed unit 14 communicates with the wall unit 16 via the communications link 22. While the bed unit 14 is capable of mobility due to its attachment to the mobile hospital bed 26, each wall unit 16 remains stationary in its associated hospital room 10a. Therefore, the wall unit 16 is able to communicate with the bed unit 14 when the bed unit 14 moves in its proximity. The wall unit 16, in turn, conveys the collected information to the health care provider 54 via the nurse call system 56. The nurse call system 56 connects a plurality of rooms 10a, 10b, each having a bed 26, 28 and a corresponding bed/wall unit pairs 14/16, and 18/20 to one or more nursing station monitors 12 for allowing the health care provider 54 to monitor the patient information. Exemplary nurse call systems include any one of a line of Responder® integrated health care communications systems manufactured by the Rauland Borg Corporation located at 3450 West Oakton Street, Skokie, Ill. 60076. In one embodiment, the nurse call system 56 integrates with an IP-based local area network to accumulate the patient information from a plurality of mobile hospital beds 26, 28 via connections 58, 60. To provide a local indication of on-going bed exit and nurse call events to the health care provider 54, the wall unit 16 additionally connects to an external room transducer 15, which is mounted to one of the internal or external walls of each room 10a and 10b. The room transducer 15 provides an audio alert, such as a speaker or a buzzer tone, for the health care provider 54 to check on the patient within the room. Alternatively, the transducer 15 provides a visual alert, such as a flashing light, or a combination of audio and visual alerts.

Figure 2:
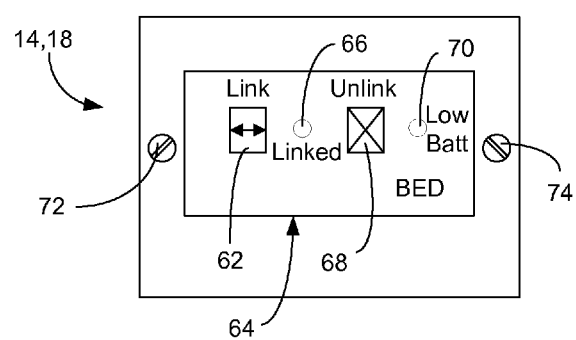
FIGS. 2 and 3 are front and side views of the bed unit of FIG. 1.
Figure 3:
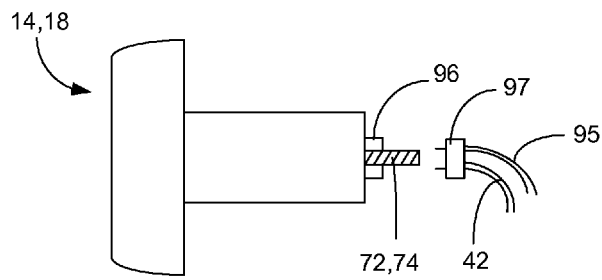

To establish the communications link 22, the health care provider interacts with user interfaces at each of the bed and wall units, such as by pressing a button on each of the units. As illustrated in FIGS. 2 and 3, to link the bed unit 14 with the wall unit 16, the health care provider presses a link button on one or both of the user interfaces 64 and 78 of the bed and wall units 14 and 16, respectively. Preferably, it does not matter whether the health care provider first presses the link button 62 or the link button 76 to initiate the linking process. Pressing a link button on either the bed unit 14 or the wall unit 16 initiates a timer during which the health care provider is required to press the corresponding link button on the other unit of the pair to be linked. In one embodiment, the linking process timer is set to five (5) seconds from the time the health care provider activates the link button 62 or the link button 76. Each unit's link indicator 66, 80 flashes during the linking process. Once the linking process is complete and the communications link 22 between the linked bed/wall unit pair is established, the wall unit's link indicator 80 lights up continuously. Since the bed unit is preferably battery operated, while the wall unit is powered through its connection to the nurse call system, the bed unit's link indicator 66 turns off to save battery power after the communications link 22 is established.

If the link attempt is unsuccessful, one or both of the bed unit 14 and the wall unit 16 sounds a continuous tone for a predetermined duration. In the illustrated embodiment, the unit that initiates the link attempt signals a failure since the other unit may not be aware of the attempt.

To immediately silence the link failure tone, the health care provider presses the bed unit's unlink button 68 and the wall unit's cancel button 82. Similarly, when the bed 26 is moved to another hospital room, the health care provider manually unlinks a linked bed/wall unit pair by pressing the unlink button 68 on the bed transceiver unit 14. Unlinking the units also generates a "bed out" signal, which the wall unit 16 relays to the nursing station monitor 12 to alert the caregiver personnel that the communications link 22 between the two units is lost. The bed unit also generates a "bed out" signal and activates the low battery indicator 70 when its battery level drops below a predetermined threshold. When the bed unit 14 is linked to the wall unit 16, the wall unit 16 similarly activates its low battery indicator 84 upon relaying the "bed out" signal and the associated low battery warning to the nursing station. The low battery threshold is preferably set so as to allow continued operation of the bed unit 14 for a number of days or weeks after the activation of the low battery indicators in order to provide the caregiver with sufficient time to change the batteries.

Preferably, the bed and wall units include a link reminder feature that alerts the health care personnel to initiate the linking process whenever an unlinked bed unit 14 moves in proximity of the unlinked wall unit 16. The bed unit 14 emits an audio reminder, such as a short chirp, to prompt the health care personnel to initiate the linking process and press the link button 62 or the link button 76. Alternatively, the wall unit 16 can provide the reminder or even both units 14 and 16 can provide reminders, including a visual reminder, such as flashing the link status LEDs 66, 80 at one or both units, instead of or in addition to the audio reminder.

If the caregiver decides that the communications link 22 should not be established between the two units, he or she presses the unlink button 68 on the bed unit 14 in order to silence the link reminder alarm. Preferably, the link reminder returns after a predetermined time, such as one hour, if the two unlinked units still remain unlinked and in proximity. However, to provide a link reminder with respect to a new pair of unlinked units, such as when a previously silenced unlinked bed unit is moved in proximity of a different unlinked wall unit, the link reminder returns before the one hour period. Additional aspects of operation of the link reminder feature are discussed in more detail below in connection with the state diagrams and flowcharts of FIGS. 13 and 19.

Figure 4:
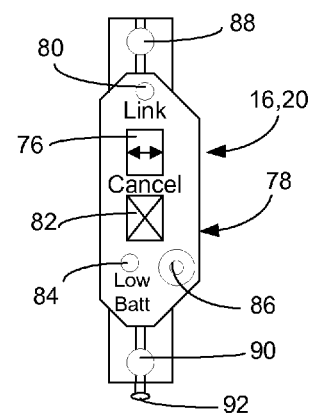
FIGS. 4 and 5 are front and side views of the wall unit of FIG. 1.
Figure 5:
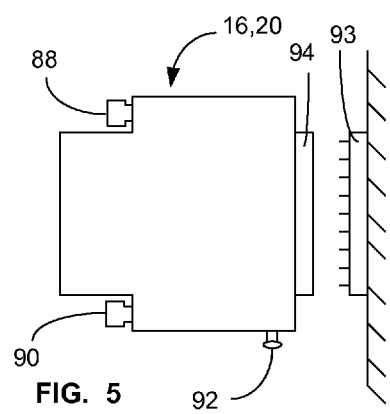

As illustrated in FIG. 4, to convey the patient information from the mobile hospital bed 26 to a nearby wall unit 16, the bed unit 14 attaches to the bed frame 34 via fasteners 72, 74 and interfaces with the bed sensor 30 and the communications module 46 via a connector 96. Specifically, the bed unit connector 96 mates with a bed interface connector 97 for routing the patient occupancy information (e.g., bed exit alarms), as well as nurse call and call assurance signaling, to the bed unit 14 via cables 42 and 95 respectively. The connector pair 96 and 97 uses a DB37 pin type connection. Similarly, as shown in FIG. 5, the wall unit 16 interfaces with the nurse call system 56 and room transducer 15 via a connector pair 93 and 94, which also employs a DB37 pin type connection. Preferably, the wall unit 16 is powered through the connector 94 via a corresponding pin connection to the nurse call system 56. To provide an alternative power source, which can be used during the maintenance of the nurse call system 56, for example, the wall unit 16 includes an external power port 86. Wall fasteners 88, 90 ensure that the connector 94 does not come loose from its wall receptacle, while the chain pin 92 provides an attachment point for a small wall chain to ensure that the wall unit 16 is not misplaced when it is disconnected from the wall receptacle, such as during the system maintenance.

Circuitry comprising each of the bed unit 14 and wall unit 16 includes radio frequency (RF) and controller components to manage the establishment and maintenance of the communications link 22. The RF component is a transceiver for supporting the wireless communications link 22. The controller component cooperates with the transceiver to support the processes described herein.

Figure 6:
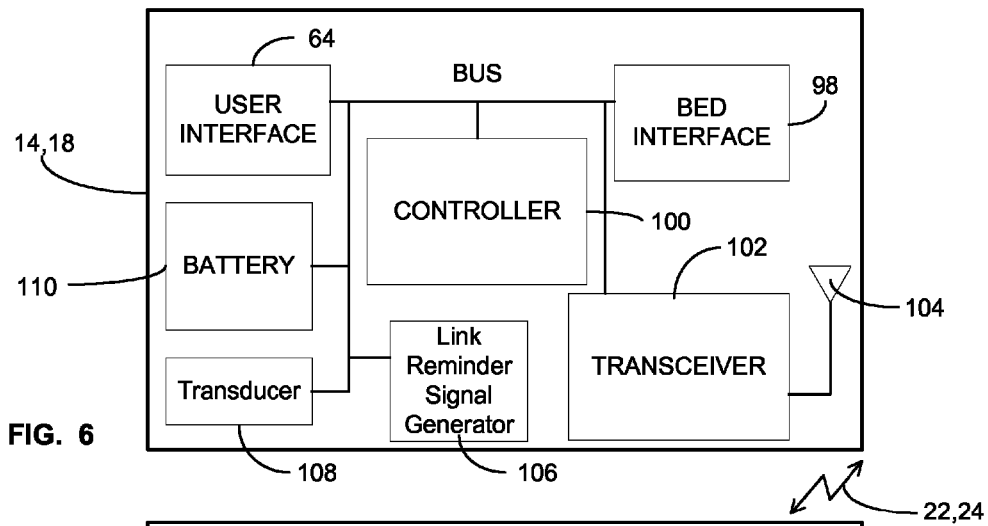
FIG. 6 is a schematic diagram of the RF and controller circuitry in the bed unit of FIGS. 1-3.
Figure 7:
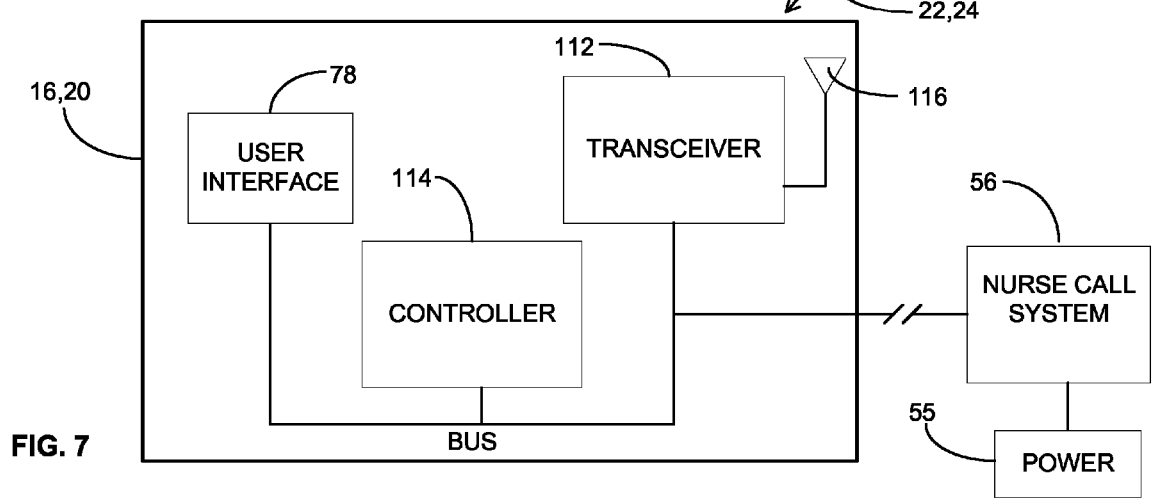
FIG. 7 is a schematic diagram of the RF and controller circuitry in the wall unit of FIGS. 1, 4 and 5.

Referring to FIGS. 6 and 7, the bed interface circuitry 98 of the bed unit 14 collects the patient information from the bed sensor 30, as well as the communications module 46 (FIG. 1), and provides it to the controller 100 for processing. In turn, the bed unit controller 100, as well as the wall unit controller 114, manage the establishment, operation, and status reporting of the communications link 22, 24, via their respective RF circuitry components, namely the transceivers 102, 112, in order to relay the collected patient information between the units and to the nurse call system 56 and/or the room transducer 15. An exemplary embodiment of the controllers 100, 114 is a model CY8C27443 manufactured by Cypress Semiconductor Corporation located at 198 Champion Ct., San Jose, Calif. 95134. An exemplary embodiment of the transceiver circuitry 102, 112 is a model XE1203F transceiver module manufactured by Semtech Corporation, located at 200 Flynn Road, Camarillo, Calif. 93012. Preferably, each of the bed and wall units 14 and 16 includes an internal antenna 104, 116, respectively, coupled to the transceiver circuitry 102, 112 for transmitting the patient information between the units.

When the bed unit 14 is in its unlinked state and its controller 100 detects a nearby unlinked wall unit 16, the controller drives the link reminder signal generator 106 by outputting an activation signal to the link reminder signal generator, which responds by generating a link reminder alarm that can be a sound generated by a transducer 108 and/or a visual prompt at the user interface 64. Although in the illustrated embodiment the link reminder signal generator 106 is external to the controller 100, the generator and the controller may be a single component. In the illustrated embodiment, the transducer 108 provides an audio alert and may be a piezoelectric buzzer that emits short chirping sounds, while other embodiments include visual link reminders at the interface 64, such as flashing LEDs, as well as combinations of audio, visual, and other types of alert indicators. In yet another embodiment, the wall unit 16 also includes the link reminder signal generator and transducer circuitry for alerting the health care personnel of its unlinked status.

In order for the communications link 22 to be a completely wireless connection, the bed unit 14 includes a local power source such as one or more batteries 110. Battery operation enables the unlinked bed unit 14 to operate continuously and without relying on hospital personnel to attach a power source. However, external power sources can also provide power to the bed unit 14. For example, power can be derived from a power source primarily intended for the bed 26. If total power consumption is very low, the bed unit 14 may even be powered by an electromagnetic source remote from the unit and the bed in a manner similar to passive transponders. When powered by batteries 110, power consumption is minimized by including a sleep mode for the electronics wherein the controller 100 periodically directs the bed unit 14 to enter a partially powered down state. Unlike the bed unit 14, however, the wall unit 16 is usually fixed in the hospital room and, therefore, has access to the hospital's primary power resources. Thus, the wall unit need not require power conservation techniques although it still may incorporate them if desired. As illustrated in FIG. 7, the wall unit 16 draws power from the nurse call system power source 55 via a pin connection at its connector interface 94 (FIG. 5).

Figure 8:
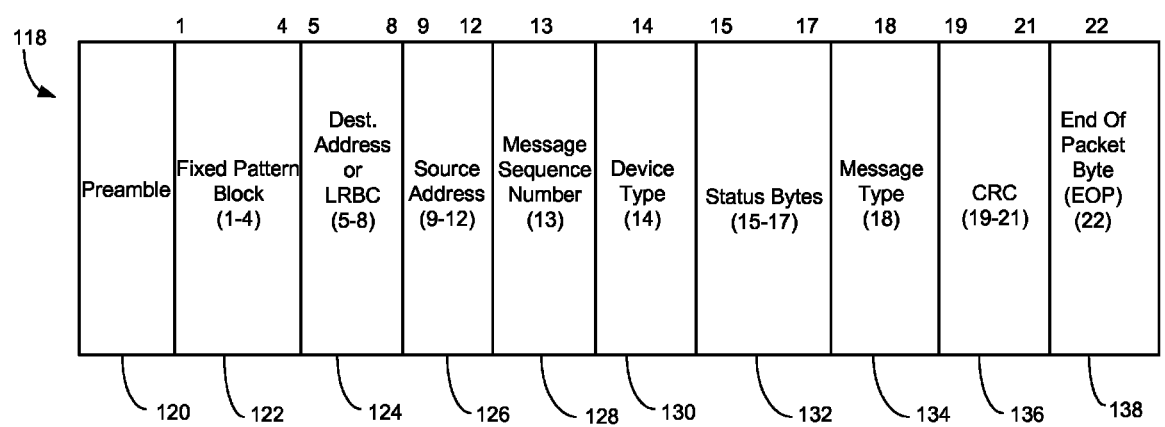
FIG. 8 illustrates the format of a communications frame in accordance with the communications protocol of the invention.

To provide for message transmission between the bed and wall units, the message format employed by the communications link 22 includes a plurality of message fields corresponding to message routing, data payload, and error detection signaling. In FIG. 8, a message packet for transmission by the communications link 22 is a message frame 118 comprising a 22 byte sequence preceded by a preamble 120 to allow the transceiver 102, 112 in each of the bed and wall units 14 and 16 to lock onto the incoming message data stream in a conventional manner. The preamble 120 is a known or expected bit sequence that the receiving bed or wall unit 14, 16 discards after locking onto the message stream. Thus, the receiving bed or wall unit 14, 16 does not include the preamble 120 in the message decoding, cyclic redundancy code (CRC), and message byte count calculations.

Proceeding down the message byte sequence, message bytes 1-4 include a fixed pattern block 122, which comprises the same four hexadecimal bytes within each message frame 118. During system testing and maintenance, the fixed pattern block 122 enables a test receiver to log all message traffic on a given channel without concern for the source address 126 in the transmission packet, which is exchanged by the bed and wall units during the establishment of the communications link 22. When a health care provider initiates the linking process by pressing the link button 68, 76 at either the bed or the wall unit 14, 16, the bed unit transmits a message packet with a Link Request Broadcast Code (LRBC) within the field 124 corresponding to bytes 5 through 8 of the message frame 118. Alternatively, when the bed and wall units 14, 16 are linked, the message field 124 includes a destination address of the bed or wall unit, depending on the originating unit, that is the address of the intended recipient of the message frame 118. During the setup of the communications link 22, the bed and wall units exchange their unique addresses, which correspond to device serial numbers. Similarly, the message field 126 (bytes 9-12) contains the source address, or serial number, of the transmitting device. Other embodiments include exchanging Media Access Control (MAC) addresses between the units to designate destination and source addresses among the devices.

To keep track of the message exchange and to identify the communicating devices, the message frame 118 includes a message sequence number counter 128 and a device type field 130 (bytes 13, 14). The message sequence number counter 128 keeps track of the message session number for the corresponding device within the communications link 22. When the communications link 22 is established between a bed/wall unit pair, the device type field 130 identifies each communicating device as a bed or wall unit, respectively. The device type field 130 also identifies additional device types when the communications link 22 includes other devices, such as a wall-mounted emergency push button station and/or a pull cord station for generating a nurse call signal.

The status bytes field 132 (bytes 15-17) relays additional message data and patient information, such as a nurse call signal indicator, a bed exit alarm indicator, a bed out alarm indicator, link reminder signaling, and various link status indicators, including periodic link status request or "check-in" signaling between the linked units. The message type field 134 (byte 18), in turn, includes "Ack" indicators sent in response to a successful receipt of certain messages, as well as "Nak" indicators sent in response to messages having CRC errors identified by comparing the received message CRC to the transmitted CRC bytes 136 (bytes 19-21). Message type field 134 also relays link connection commands between the bed and wall units. As discussed in more detail in connection with FIG. 12 below, the transmission protocol also provides advanced collision detection by monitoring for corruption of the last byte (byte 22), called the end-of-packet (EOP) or "tail feather" byte 138, in transmission of Ack messages sent in response to periodic check-in messages. The tail feather byte 138 is not used to calculate the CRC value. Therefore, Ack messages having good CRC values and uncorrupted data payloads, but having a corrupted tail feather byte 138, provide an early indication of collisions of periodic check-in message sequences between multiple bed/wall unit pairs. Upon detection of corruption of the tail feather byte 138, the transmission protocol includes time or frequency shifting the next periodic transmission of check-in or link status messages by a random delay in order to prevent data corruption.

To reduce the overall number of messages exchanged between the linked bed/wall unit pairs and, consequently, extend each bed unit's battery life, the message protocol further provides for transmission of full frames at all times between both units within the pair, including when the message type byte 134 contains an Ack or a Nak indicator. This allows inclusion of additional data within the message frames containing the Ack or Nak signaling, thereby reducing the need for separate data transmissions.

Figure 9:
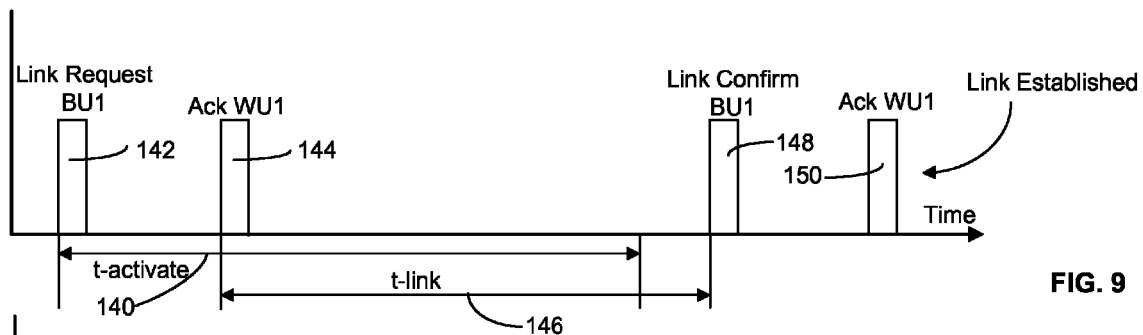
FIG. 9 is a timing diagram illustrating the successful completion of the linking process to establish a communications link between a bed/wall unit pair of FIG. 1.
Figure 10:
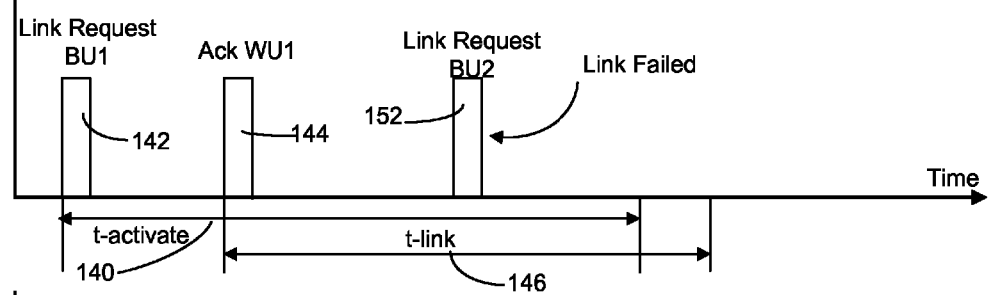
FIGS. 10 and 11 are timing diagrams illustrating different scenarios leading to failure of the linking process of FIG. 9.
Figure 11:
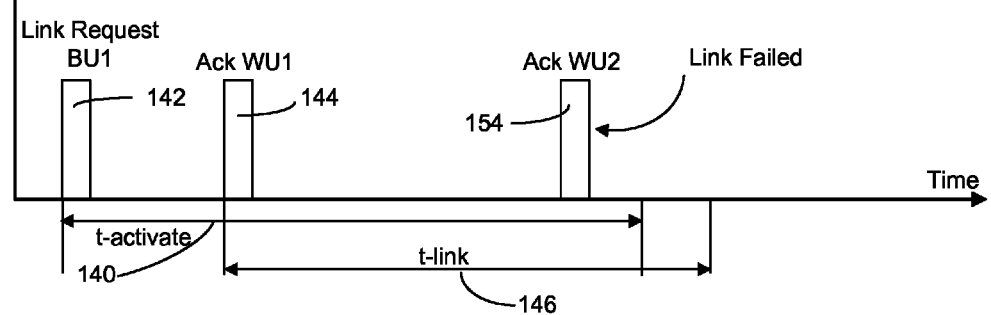

The timing diagrams of FIGS. 9-11 are exemplary scenarios related to establishing the communications link 22. FIG. 9, for example, depicts a transmission protocol that results in successfully establishing the communications link 22, where the health care provider initiates the linking process by pressing each of the link buttons 62, 76 on the bed/wall unit pair 14/16 within a predetermined amount of time 140. The timer 140 is set to allow the health care provider sufficient time, such as five (5) seconds, to press the link button on the second unit after pressing the link button on the first unit. During this time period, the bed unit 14 transmits a link request broadcast code (LRBC) 142, labeled "Link Request BU1" to indicate a link request from a first bed unit, and waits to receive an acknowledgment 144, labeled "Ack WU1" to indicate an acknowledgement from a first wall unit, from a nearby wall unit 16.

Since the bed and wall units 14, 16 exchange their unique addresses to establish the communications link 22, the bed unit is initially unaware of which wall unit will reply to its link request. Therefore, when the communications link 22 is between only one wall unit and one bed unit, it is desirable to prevent the occurrence of inadvertently cross linking the pairs of units in two different rooms 10a and 10b (FIG. 1). For example, if the two bed units 14, 18 in the adjacent hospital rooms 10a, 10b initiate the linking process at about the same time, there is an opportunity for each of the units to link to the wall unit in the other room. Therefore, after exchanging their unique addresses included in the initial link request broadcast code and acknowledgement messages 142, 144, the bed and wall units 14, 16 wait for another predetermined duration 146 in FIG. 9 to receive link requests or acknowledgements from other nearby units, such as the units 18 and/or 20 in the other room in FIG. 1, in order to ensure that cross linking of two pairs of units has not occurred.

In one embodiment, the timer 146 is also set to five (5) seconds. If the timer 146 expires without detection of a link request or an acknowledgement having an address different from either of the original addresses within the pair 14, 16, the communications link is established after the bed unit 14 transmits a link confirmation message 148 and receives an acknowledgement 150 from its corresponding wall unit 16. Otherwise, the link fails when, prior to the expiration of the linking timer 146, the wall unit 16 receives a link request 152 having a bed unit address different from that in the original link request 142 (FIG. 10), or when the bed unit 14 receives an acknowledgement 154 having a wall unit address different from that in the original acknowledgment 144 (FIG. 11).

Instead of establishing one-to-one communication links 22 between bed and wall units, the communications link can also be one-to-many in that one of the wall units 16 can support communications links 22 to several bed units 14. In this case, when the health care provider presses the wall unit's 16 link button, the wall unit sends out a periodic linking beacon message and listens for reply messages from one or more nearby bed units 14 once the health care provider presses their corresponding link buttons. In this scenario, the wall unit 16 remains in the linking mode for a predetermined duration, such as 5 seconds, during which it listens for bed unit replies.

Upon receipt of one or more bed unit reply messages, the wall unit 16 sends out link confirmation messages addressed specifically to each of the bed units 14 that replied, thereby forming multiple bed/wall unit pairs 14, 16, where all of the communications links 22 have a common wall unit and a unique bed unit. In this embodiment, to prevent cross linking the bed units 14 with more than one wall unit, such as when multiple wall units 16 are located in adjacent hospital rooms, each of the bed units 14 fails the linking process if it receives linking beacon messages from more than one wall unit 16.

Figure 12:
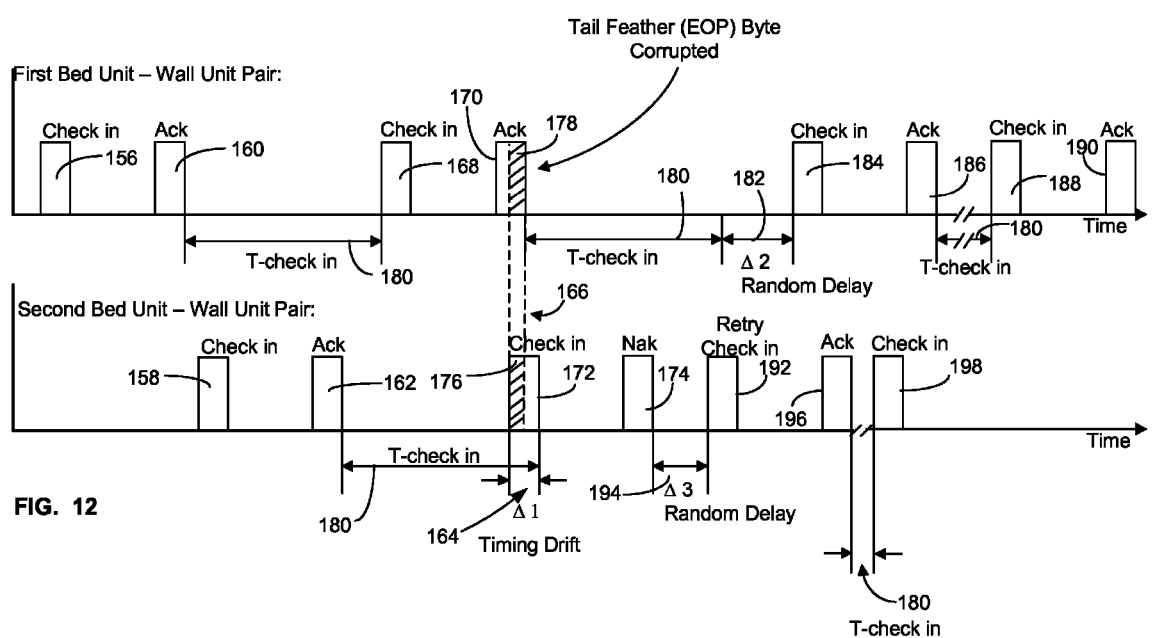
FIG. 12 is a timing diagram illustrating the adjustment of a time window in which a bed unit of FIGS. 1-3 periodically communicates with its mated wall unit to maintain the communications link, where the time window is adjusted pursuant to advanced detection of collisions of check-in message sequences associated with a bed/wall unit pair of FIG. 1.

Once the bed and wall units 14, 16 are linked, the units periodically exchange check-in message sequences in order to check the integrity of the communications link 22 between the units. When multiple linked pairs of units are in proximity, such as when a bed/wall unit pair 14, 16 in hospital room 10a is adjacent to another linked bed/wall unit pair in room 10b, each pair of units undergoes its own periodic exchange of check-in message sequences, as illustrated in FIG. 12.

Either the bed unit 14 or the wall unit 16 may originate the periodic check-in message transmissions, though it is preferable in this embodiment for the bed unit to initiate all communications. Since the bed unit 14 is preferably battery operated, its transceiver circuitry 102 is temporarily powered down to save battery power after its communications link 22 is established. In the absence of other transmissions, such as bed exit and/or bed out alarms, the controller 100 of each bed unit 14 periodically wakes up the transceiver circuitry 102 to ensure the communications link 22 is alive at the other unit by sending a check-in message 156, 158 (FIG. 12) to its corresponding wall unit 16 and waiting for the subsequent acknowledgement (Ack) message 160, 162 from its wall unit 16.

There is a tendency for the endpoints of the periodic check-in and Ack message transmissions in one link 22 to gradually drift in time with respect to the same signals in another link due to inherent differences in each unit's timing circuitry. This gradual drift 164 in the check-in message transmissions, for example, in a communications link 22 may result in a message collision 166 due to a temporal overlap between the end of one of the periodic check-in transmission sequences 168, 170 for one pair and the beginning of a corresponding check-in transmission sequence 172, 174 for another co-channel pair. Therefore, the message protocol provides advanced collision detection by monitoring for corruption of the end-of-packet (EOP) or "tail feather" byte 138 (FIG. 8), in transmission of messages from the wall unit 16.

Specifically, when the bed unit 14 receives an Ack message 170 from the mated wall unit 16 with good CRC but with a corrupted EOP byte 138, the message protocol assumes the leading edge 176 of another check-in message 172, belonging to a different communications link 22, is beginning to overlap the trailing edge 178 of the Ack message 170. Since all linked bed units 14 normally transmit the initial check-in messages at a fixed period 180 in FIG. 12, there is a high probability that the collision will reoccur during the next periodic transmission of the check-in message sequences in each of the links 22. To prevent reoccurrence of collisions, the bed unit 14 that detected the corrupted EOP byte 138 adds a one-time random delay interval 182 to its next check-in period 180, thereby permanently shifting the nominal time slot of its periodic check-in message sequences with respect to another bed/wall unit pair. After the random delay 182, transmissions of check-in message sequences 184, 186 and 188, 190 continue according to the original check-in period 180. While the illustrated embodiment allocates a single byte 138 for the EOP marker, other embodiments include allocating a plurality of EOP bytes at the tail end of the message frame 118 (FIG. 8) in order to enhance the ability to detect another impending collision before the data payload is affected.

In the scenario illustrated in FIG. 12, the collision 166 corrupted the data payload within the leading edge of the check-in message 176, thereby resulting in a CRC error at the corresponding wall unit. To indicate a CRC error, the wall unit 16 receiving the corrupted check-in message 176 transmits a Nak message 174. Upon receipt of the Nak message 174, the bed unit 14 within this pair initiates a retry transmission of the check-in message 192 after a random delay 194. In this case, the bed unit receives an Ack message 196, indicating a successful receipt of the check-in message 192 by its corresponding wall unit 16. In this illustrated embodiment, unlike the situation in which a message is received having good CRC but corrupted EOP or tail feather byte 138, which provide an early indication of a collision prior to data corruption, when the bed unit 14 receives a transmission having bad CRC or including a Nak message, it resends the check-in message after a random delay 194. In this case, however, the bed unit 14 does not add the random delay 194 to the next check-in message period 180. In other words, the bed unit 14 still transmits the next check-in message 198 after a check-in period 180 referenced from the corrupted check-in message 172. In this case, the bed unit does not change its nominal time slot for subsequent check-in message transmissions because the CRC error also could have been caused by reasons other than a collision with another bed/wall unit pair's periodic check-in message sequence, such as due to a signal fade.

In addition to detecting gradual collisions by monitoring corruption of the end-of-packet byte, the communications link 22 is also managed so that the bed unit's nominal time slot for transmission of periodic check-in messages is monitored for sudden collisions. The monitoring detects successive occurrences of check-in message retries followed by successful receipt of Ack messages. This method of check-in message time slot management detects a sudden and recurring collision of check-in message sequences that occur after one of the bed/wall unit pairs resets its check-in message period 180 due to transmission of nurse call or bed exit signaling. Specifically, a collision between the check-in messages of two nearby bed units results in a bad CRC to either or both pairs of units. In this case, either or both bed units 14 in the two communications links 22 receive a Nak message from their corresponding wall units or do not receive any reply at all. This prompts the bed unit 14 to retry the transmission of the check-in message after a random delay. If the second transmission of the check-in message is successful, the bed unit 14 receives an Ack message from the wall unit 16 in response. The combination of first-try failure of the check-in sequence and first-resend success is a strong indication of colliding bed units 14 since other possible causes of packet corruption are not likely to appear and disappear quickly. Therefore, each bed unit 14 keeps a count of successive occurrences of the combination of successive first-try failures followed by first-resend successes. If this count reaches a predetermined limit, such as 3 such combinations for example, the bed unit makes a permanent shift in its nominal check-in message sequence time slot by adding a random delay to its next periodic check-in message transmission.

In response to detection of check-in message sequence collisions among multiple communications links 22, whether via detection of EOP byte corruption or via monitoring the described combination of successive first-try check-in message failures followed by first-resend successes, at least one of the bed/wall unit pairs whose communications link 22 is colliding initiates a change in its operating channel frequency to avoid future collisions.

Figure 13:
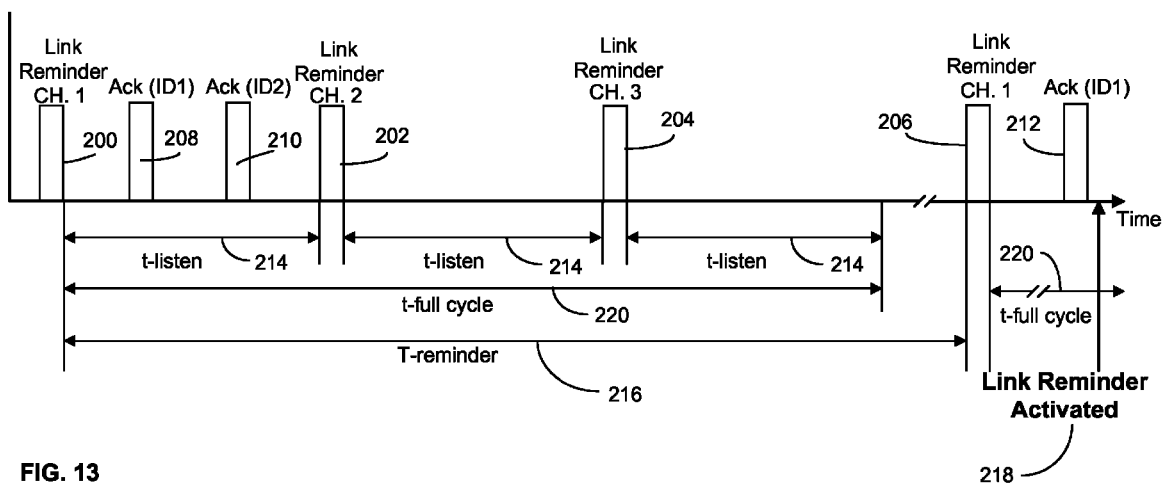
FIG. 13 is a timing diagram illustrating the operation of the link reminder to alert the health care provider to initiate the linking process of FIG. 9.

Turning to FIG. 13, should a communications link 22 fail or the responsible hospital personnel forgets to link the two nearby bed and wall units 14, 16, one of the unlinked units sends out periodic link reminder messages to the other nearby unlinked unit(s) on each of the multiple operating channels and listens for corresponding acknowledgement (Ack) messages from one or more other unlinked units. Preferably, the bed unit 14 sends out the link reminder messages 200-206 on each of the system operating channels and logs the wall IDs, or wall unit serial numbers, from which it receives acknowledgement replies 208-212 in the memory of its controller 100. Since the bed unit 14 is battery operated where its transceiver circuitry 102 periodically enters an idle sleep mode, the bed unit includes a periodic reminder timer 216 to wake up its transceiver circuitry and begin the link reminder message cycle 220. In this embodiment, the system operates on 3 channels, therefore during each link reminder message cycle 220 the bed unit 14 transmits the link reminder messages 200-204 on each operating channel because the bed unit 14 is not aware of the current operating channel of a nearby unlinked wall unit. Transmission of link reminder messages on multiple operating channels also takes into account possible collisions with other nearby bed units in the link reminder mode. Pursuant to each transmission of link reminder messages 200-206, the bed unit 14 listens for incoming acknowledgement messages 208-212 for a corresponding listen period 214, which, in one embodiment, is set to 100 milliseconds. Once the full 3 channel cycle 220 is complete, the bed unit resumes transmitting additional link reminder messages 206 during another link reminder message cycle 220, which begins when the periodic reminder cycle 216 expires. In embodiments, the periodic reminder cycle 216 is set to 45 and 60 seconds, respectively. When the bed unit 14 detects a second acknowledgment message 212 originating from the same wall ID or serial number as one of the previous acknowledgments 208, the bed unit 14 activates the link reminder alert 218 to prompt the caregiver to initiate the linking process.

Figure 14:
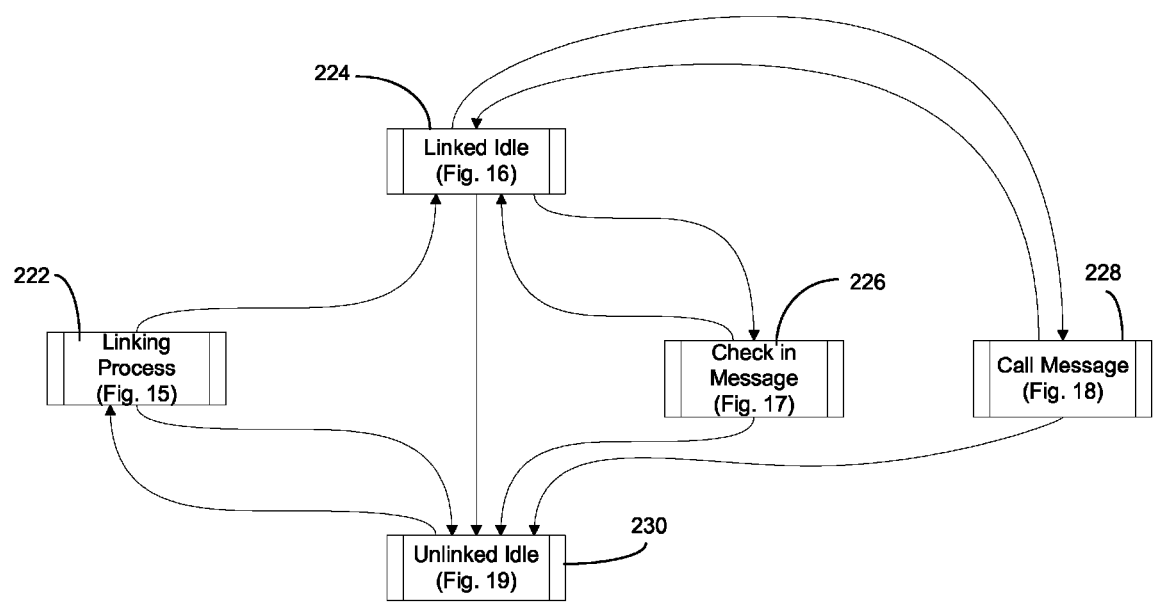
FIG. 14 is a state diagram showing the relationship among various operating states of the bed and wall units, including Linking Process, Linked Idle, Check-in Message, Call Message and Unlinked Idle states.

FIGS. 14-19 illustrate the detailed operation of embodiments of various operating states of the system in accordance with the invention. Specifically, FIG. 14 is a state diagram generally illustrating the transition between various operational states of each bed/wall unit pair, while FIGS. 15-19 are flowcharts illustrating the operation of each of the states in FIG. 14 in more detail. FIGS. 15-19 simultaneously depict operation of the bed and wall units by representing the steps associated with the bed unit on the left side, while representing the steps associated with the wall unit on the right side of each figure. It should be noted that the steps referenced throughout FIGS. 15-19 are performed by programmable firmware of each unit's controller 100, 114 (FIGS. 6 and 7).

As illustrated in FIG. 14, after going through the linking process state 222, the linked bed/wall unit pair enters the linked idle state 224 where the bed unit enters into the linked idle sleep mode by temporarily powering down its transceiver circuitry to extend the battery life when no patient information is transmitted, while the wall unit enters into a linked idle receive mode to continuously listen for messages from one or more of its associated bed units. When the linked bed/wall unit pair needs to communicate patient information, such as bed exit alarms or bed out calls, the units enter the call message state 228 to relay the information to the nurse call system. Upon completion of the call message transmissions, the units reenter the linked idle state 224. Similarly, during periodic check-in message sequences, the linked unit pair enters the check-in message state 226 and returns to the linked idle state 224 when check-in message transmission is successful. However, when the communications link 22, 24 is lost or when the linking process fails, the bed and wall units enter the unlinked idle mode, which includes periodic link reminder alerts to prompt the health care provider to (re)establish the communications link 22, 24.

Figure 15:
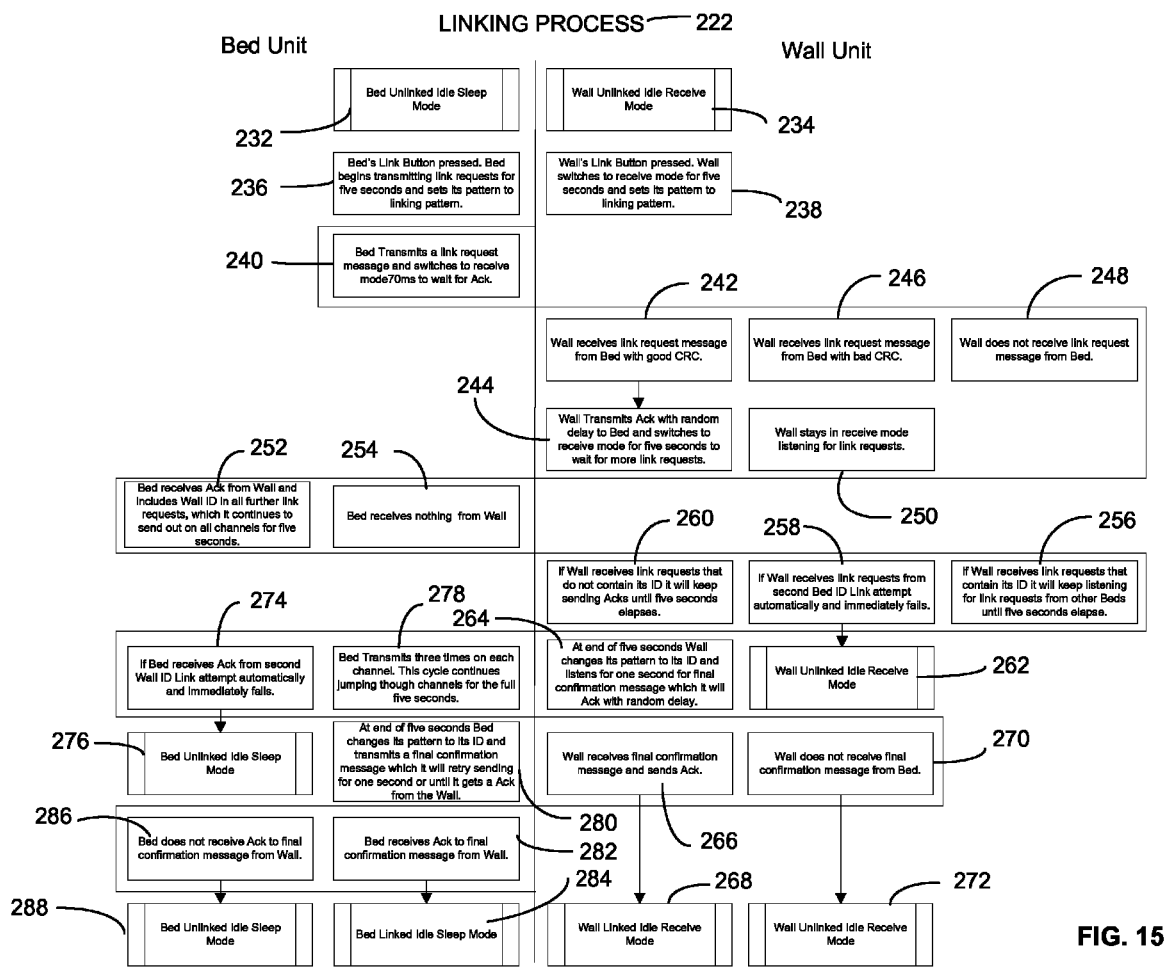
FIG. 15 is a flowchart illustrating the detailed operation of the Linking Process State of FIG. 14.

Turning to FIG. 15, detailed operation of an embodiment of the linking process state 222 is illustrated, wherein the bed unit initially powers down its transceiver circuitry in its unlinked idle sleep mode 232, while the wall unit is in the unlinked idle receive mode 234 for receiving link reminder messages from the bed unit. When the health care provider activates the bed unit's link button, the bed unit begins transmitting link request (LRBC) messages for a predetermined duration, such as five (5) seconds, step 236. Similarly, in step 238, when the health care provider activates the wall unit's link button, the wall unit listens for the bed unit's link request messages for the five (5) second period. It should be noted that after transmitting a link request message, the bed unit switches to receive mode, for example for 70 milliseconds, to wait for an Ack message from a receiving wall unit, step 240. If, in step 242, the wall unit receives a link request message with good CRC, in step 244, the wall unit transmits an Ack with random delay to the bed unit and switches to receive mode for another five seconds to wait for additional link requests from nearby bed units undergoing the linking process. As discussed above in connection with FIGS. 9-11, detection of additional bed/wall unit pairs simultaneously undergoing the linking process with the current pair, as well as the associated link failure, prevents unintended cross linking of the units located in adjacent rooms. Alternatively, in step 246, when the wall unit receives a link request message with a CRC error, or, in step 248, when the wall unit does not receive any link request messages from the bed unit, the wall unit continues to listen, in step 250, for the bed unit's link requests for the duration of its link button activation timer 238.

Correspondingly, in step 252, when the bed unit receives a first Ack message from a given wall unit, it includes the associated wall ID or serial number in all subsequent link request messages, which the bed unit continues to send out on all operating channels for another five seconds. Alternatively, in step 254, the bed unit does not yet receive any acknowledgments from the nearby wall unit(s).

If, in step 256, the wall unit receives link request messages that include its ID or serial number in the destination address field, it continues listening for link request messages originating from bed unit IDs other than the source of original link request message until the expiration of the linking period timer 244. Specifically, in step 258, if the wall unit receives a link request, containing its ID in the destination field, from a second bed unit ID designated as the source device, the link attempt immediately fails and the wall unit enters the unlinked idle receive mode, step 262, to prevent unintended cross linking of multiple bed/wall unit pairs. Alternatively, in step 260, if the wall unit receives link request messages that do not contain its ID in the destination device field, the wall unit continues sending Ack messages until the 5 second linking period timer 244 expires. In step 264, at the end of the five second linking period timer 244, the wall unit listens for an additional second for a link confirmation message from the original bed unit and, in step 266, sends the corresponding acknowledgement message to establish the communications link and enters the linked idle receive mode, step 268. Otherwise, if the wall unit does not receive the final link confirmation message, step 270, the wall unit reenters the unlinked idle receive mode in step 272.

As with the wall unit, if, in step 274, the bed unit receives an Ack message from a second wall unit ID designated as the source device, the link attempt immediately fails and the bed unit enters an unlinked idle sleep mode, step 276, to prevent unintended cross linking of multiple bed/wall unit pairs. Otherwise, in step 278, the bed unit continuously transmits link request messages three (3) times on each of the operating channels until the expiration of the five (5) second timer 252. At the end of the five (5) second timer 252, the bed unit transmits a final link confirmation message and awaits a corresponding Ack message from the wall unit, step 280. To ensure successful completion of the linking process, the bed unit is able to retry transmission of the final link confirmation message until it receives an acknowledgement from the wall unit. Once the bed unit receives the acknowledgement to the link confirmation message, step 282, the bed unit enters the linked idle sleep mode in step 284 where it temporarily powers down its transceiver circuitry until either receiving patient information, such as bed out and bed exit alarms, or until the next periodic transmission of check-in messages. Otherwise, in steps 286, 288, the bed unit enters the unlinked idle sleep mode where it initiates periodic link reminder messages and link reminder alerts to prompt the health care provider to reinitiate the linking process with a nearby unlinked wall unit.

Figure 16:
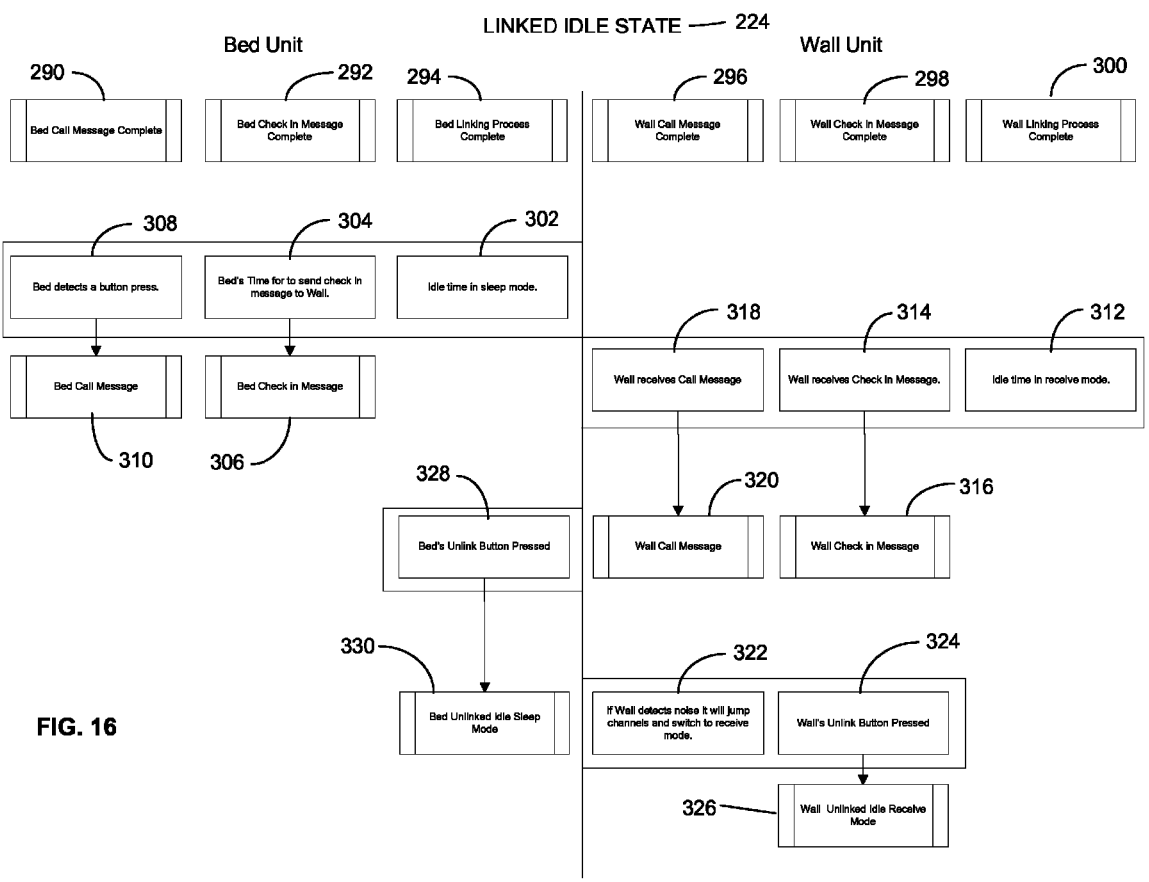
FIG. 16 is a flowchart illustrating the detailed operation of the Linked Idle State of FIG. 14.

Turning to FIG. 16, detailed operation of an embodiment of the linked idle state 224 is illustrated. The bed/wall unit pair enters the linked idle state 224 after successful completion of the linking process and pursuant to successfully relaying the patient information between the units, including the nurse call signaling initiated by the patient, bed exit and bed out alarms, as well as periodic check-in or link status message transmissions, steps 290-300. In this case, the bed unit remains in a linked idle sleep mode 302 wherein it temporarily powers down its transceiver circuitry until it is time to transmit periodic check-in messages to the wall unit, steps 304, 306, or the bed unit needs to relay the patient information to the wall unit, for example when the bed unit detects that the patient activated a nurse call button via the siderail communications module, steps 308, 310.

Correspondingly, the wall unit remains in the idle receive mode 312 where it listens for bed unit transmissions and subsequently enters the check-in message state, steps 314, 316, or the call message state, steps 318, 320, upon receipt of periodic check-in messages or other patient information from the wall unit. It should be noted that, in step 322, the wall unit monitors noise on its operating channel in order to detect and evade interference from other bed/wall units, as well as from other devices occupying the same spectrum, such as cordless phones operating in Direct Sequence Spread Spectrum mode, for example. Therefore, in this embodiment, if the wall unit detects noise after a few consecutive noise readings, it moves to the next operating channel and switches to receive mode, while waiting for the linked bed unit to attempt a new transmission, accumulate a plurality of Missed Wall Unit events, and rejoin the wall unit on the new channel. Finally, when the health care provider activates the unlink button at either unit, the bed unit enters the unlinked idle sleep mode, where it periodically wakes up its transceiver circuitry to send out the link reminder messages to nearby unlinked wall units, while the wall unit enters the unlinked idle receive mode to listen for the bed unit's link reminder transmissions, steps 324-330.

Figure 17:
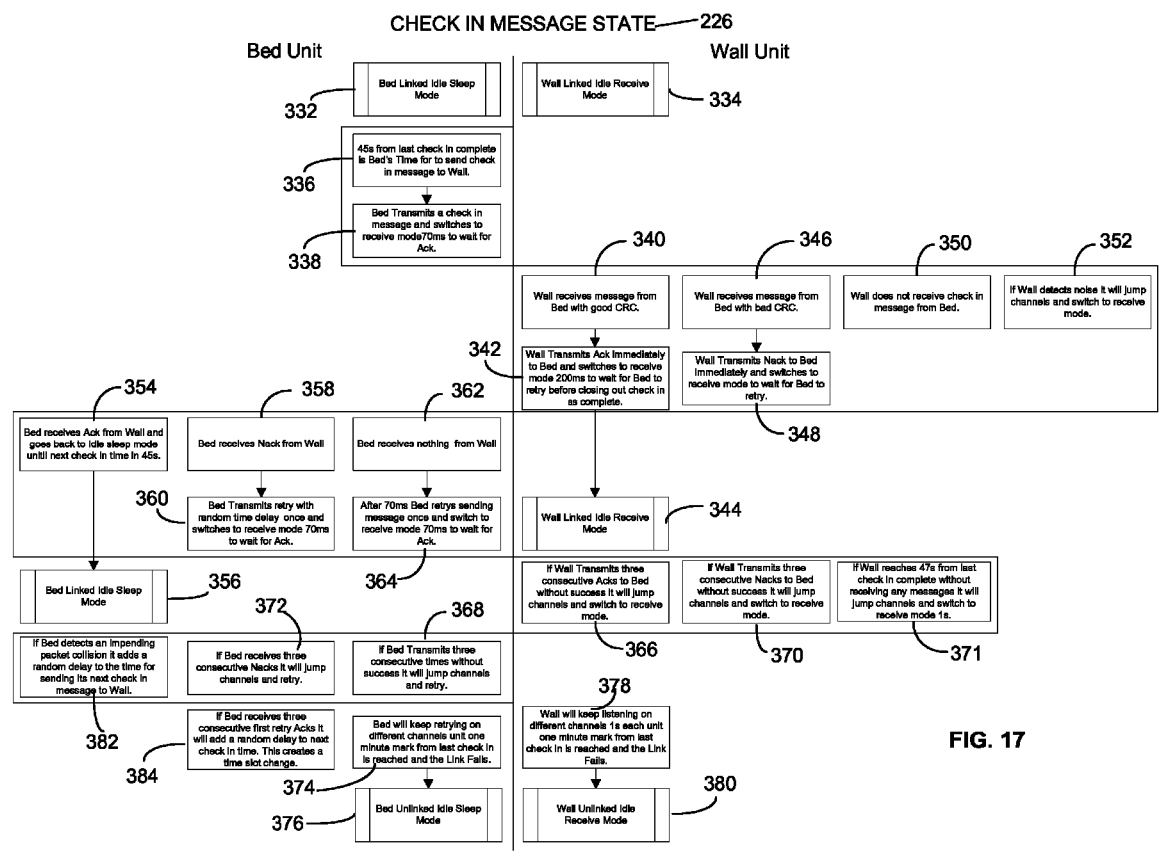
FIG. 17 is a flowchart illustrating the detailed operation of the Check-in Message State of FIG. 14.

Turning to FIG. 17, detailed operation of an embodiment of the check-in message state 226 is illustrated. In this embodiment, when the linked bed/wall units are in their respective linked idle modes, steps 332, 334, the bed unit periodically transmits check-in, or link status, messages to the associated wall unit and temporarily switches to receive mode in order to await for corresponding acknowledgments from the wall unit, steps 336, 338. In an embodiment, the bed unit periodically transmits the check-in messages every 45 seconds and thereafter switches to the receive mode for a 70 millisecond duration.

If the wall unit receives a check-in message with good CRC value, the wall unit transmits an Ack message and, in this embodiment, listens for another 200 milliseconds for any incoming retry transmissions from the bed unit prior to completing the check-in process by returning to the linked idle receive mode until the onset of the next check-in message period in 45 seconds, steps 340-344. Alternatively, if the wall unit receives a check-in message having a CRC error, the wall unit replies with a Nak message and listens for subsequent retry transmissions by the bed unit, steps 346, 348. In yet another scenario, if the wall unit does not yet receive the check-in message, whether due to poor RF conditions or otherwise, the wall unit remains in the linked idle receive mode to await the incoming check-in message transmission, step 350. During the check-in message state, the wall unit also monitors the current channel for noise conditions and, upon detecting presence of RF noise, the wall unit changes the operating frequency, step 352.

When the bed unit receives an Ack message indicating successful receipt of the check-in message by the wall unit, the bed unit returns to the linked idle sleep mode until the next check-in message period, steps 354, 356. Alternatively, if the bed unit receives a Nak message from the wall unit, indicating a CRC error in a check-in message received by the wall unit, the bed unit retries the transmission of the check-in message after a random delay after the receipt of the Nak message and awaits for a successful acknowledgement, steps 358, 360. Further, if the bed unit does not receive any reply messages from the wall unit, the bed unit retries transmitting another check-in message and listens for wall unit's replies, steps 362, 364.

In this embodiment, upon transmitting three (3) consecutive acknowledgements to the same bed unit within the check-in period, the wall unit changes to another operating channel, step 366, since repeated retries of check-in message transmission by the bed unit indicate a reception problem at the bed unit. Similarly, if the bed unit transmits three (3) consecutive check-in message retries without receiving an Ack from the wall unit, the bed unit changes to another operating channel to retry the transmission since the wall unit already moved to a different channel after transmitting three (3) consecutive Ack messages missed by the bed unit, step 368. Signal degradation at the wall unit is the likely reason for the wall unit transmitting 3 consecutive Nak messages to the same bed unit within the same check-in message period without receiving a check-in message with a good CRC value. In this case, the wall unit moves to another operating channel and switches to receive mode to listen for check-in messages from the bed unit once it follows the wall unit to the new channel, step 370. The wall unit also moves to another channel if it is overdue for receiving the next periodic check-in message transmission, such as when the periodic check-in timer has expired by two (2) seconds, step 371.

In step 372, the bed unit receives 3 consecutive Nak messages and follows the wall unit by moving to another one of the operating channels to retry the transmission of check-in messages. The bed unit repeats transmission on each new channel until it finds the wall unit's channel by receiving an acknowledgment message. Otherwise, the bed unit retries transmitting the check-in messages on different channels until some predetermined time from last receiving an Ack message. In one embodiment, the communications link fails and the bed unit enters the unlinked idle sleep mode when 60 seconds elapse from receipt of the last Ack message, steps 374, 376. Similarly, the wall unit listens for bed unit's check-in messages for one (1) second on each of the operating channels until the expiration of the one minute timer. Thereafter, the wall unit enters the unlinked idle receive mode, steps 378, 380.

As discussed above in connection with FIG. 12, to provide for early detection of check-in message collisions between check-in message sequences of multiple bed/wall unit pairs and prevent data corruption, the bed unit shifts its nominal time slot for periodic transmission of check-in messages by adding a random delay to the next scheduled check-in message transmission when it detects corruption of the end-of-packet byte in acknowledgement messages having good CRC values, step 382. Additionally, the bed unit shifts its nominal time slot for transmission of periodic check-in messages by monitoring for successive occurrences of check-in message retries followed by successful receipt of Ack messages. This method of check-in message time slot management detects a sudden and recurring collision of check-in message sequences, which occur after one of the bed/wall unit pairs resets its check-in message timer due to transmission of nurse call or bed exit signaling. In this embodiment, if the bed unit receives 3 consecutive Ack messages in response to three (3) consecutive retries of check-in message transmissions, the bed unit similarly shifts its nominal check-in message time slot by adding a random delay to the next periodic check-in message transmission time, step 384.

Figure 18:
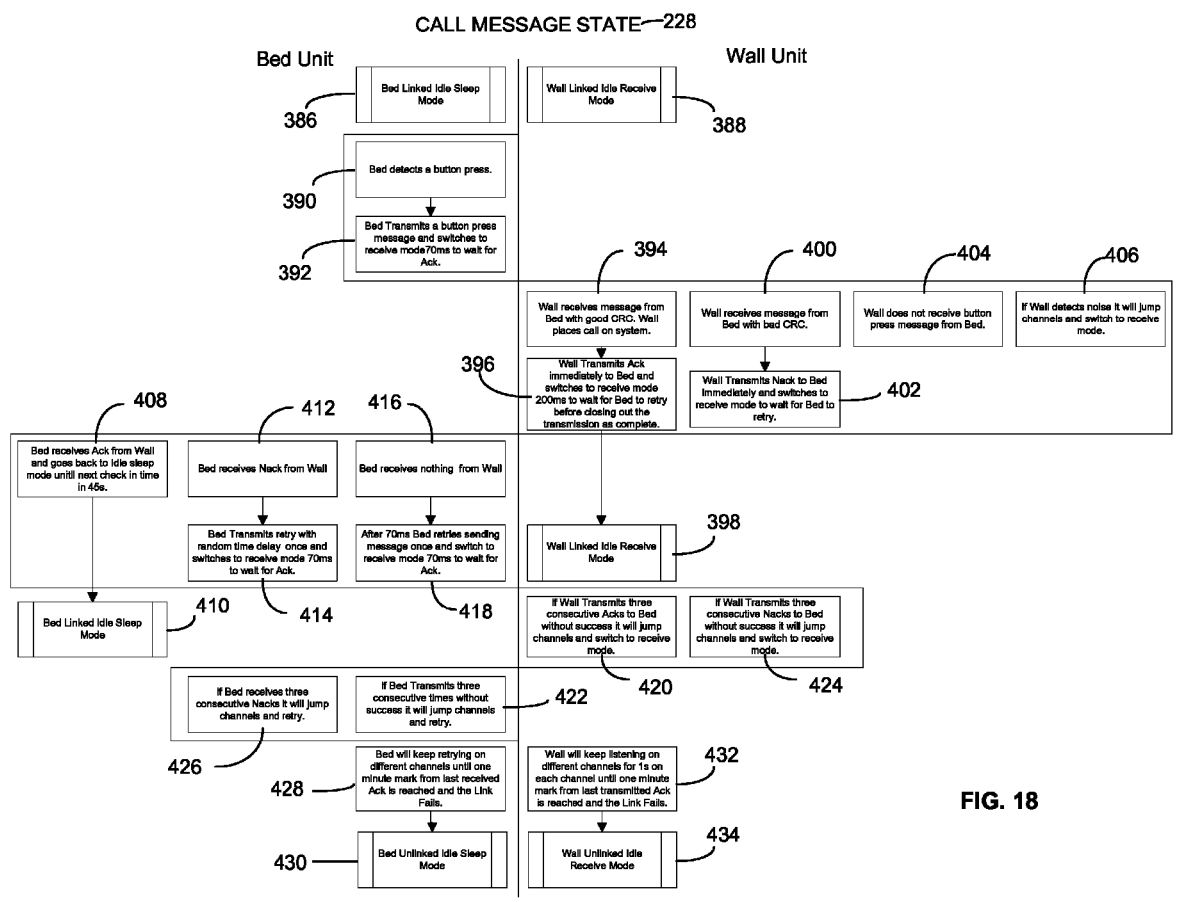
FIG. 18 is a flowchart illustrating the detailed operation of the Call Message State of FIG. 14.

Turning to FIG. 18, detailed operation of an embodiment of the call message state 228 is illustrated. In the illustrated embodiment, the linked bed/wall unit pair relays patient-initiated nurse call signaling to the hospital nurse call system, however it should be understood that the following steps also apply to transmission of other patient information, including bed out and bed exit alerts. While the linked bed/wall unit pair is in the linked idle mode, steps 386, 388, the bed unit detects activation of the nurse call button and transmits the nurse call message to the associated wall unit, steps 390, 392.

If the wall unit receives the nurse call signal with good CRC, the wall unit places a call on the nurse call system, transmits an Ack message, and listens for another 200 milliseconds for any incoming retry transmissions from the bed unit in case the bed unit does not receive the Ack message due to a signal reception problem, steps 394, 396. If the wall unit does not receive a retry transmission from the bed unit, the wall unit completes the transmission process by returning to the linked idle receive mode, steps 398. Alternatively, if the wall unit receives a nurse call message having a CRC error, the wall unit replies with a Nak message and listens for subsequent retry transmissions by the bed unit, steps 400, 402. If, however, the wall unit does not yet receive any message, whether due to poor RF conditions or otherwise, the wall unit remains in the linked idle receive mode, step 404. While in the call message state, the wall unit also monitors the current channel for noise conditions and, upon detecting presence of RF noise, changes the operating frequency, step 406.

When the bed unit receives an Ack message, the bed unit returns to the linked idle sleep mode until either the next check-in message period or the next transmission of patient information between the linked units, steps 408, 410. Alternatively, if the bed unit receives a Nak message from the wall unit, indicating a CRC error, the bed unit retries the transmission of the nurse call message with a random delay after the receipt of the Nak message and awaits for a successful acknowledgement, steps 412, 414. Further, if the bed unit does not receive any reply messages from the wall unit, the bed unit retries transmitting another nurse call message and listens for the wall unit's replies, steps 416, 418.

Upon transmitting three (3) consecutive acknowledgements to the bed unit, the wall unit changes to another operating channel, step 420, since repeated retries by the bed unit indicate that it is having a reception problem. Similarly, if the bed unit transmits three (3) consecutive retries without receiving an Ack from the wall unit, the bed unit changes to another operating channel since the wall unit already moved to a different channel after transmitting three (3) consecutive Ack messages missed by the bed unit, step 422. Signal degradation at the wall unit is the likely reason for the wall unit transmitting three (3) consecutive Nak messages to the same bed unit without receiving a message with a good CRC value. In this case, the wall unit moves to another operating channel and switches to receive mode to listen for retry messages from the bed unit when it follows the wall unit to the new channel, step 424. Thus, in step 426, the bed unit follows the wall unit when it receives three (3) consecutive Nak messages and moves to another one of the operating channels to retry the transmission. The bed unit repeats transmission on each new channel until it finds the wall unit's channel by receiving an acknowledgment message. Otherwise, the bed unit retries transmitting the messages on different channels until some predetermined time from last receiving an Ack message. In one embodiment, the communications link fails and the bed unit enters the unlinked idle sleep mode when 60 seconds elapse from receipt of the last Ack message, steps 428, 430. Similarly, the wall unit listens for the bed unit's message for one (1) second on each of the operating channels until the expiration of the one minute timer. Thereafter, the wall unit enters the unlinked idle receive mode, steps 432, 434.

Figure 19:
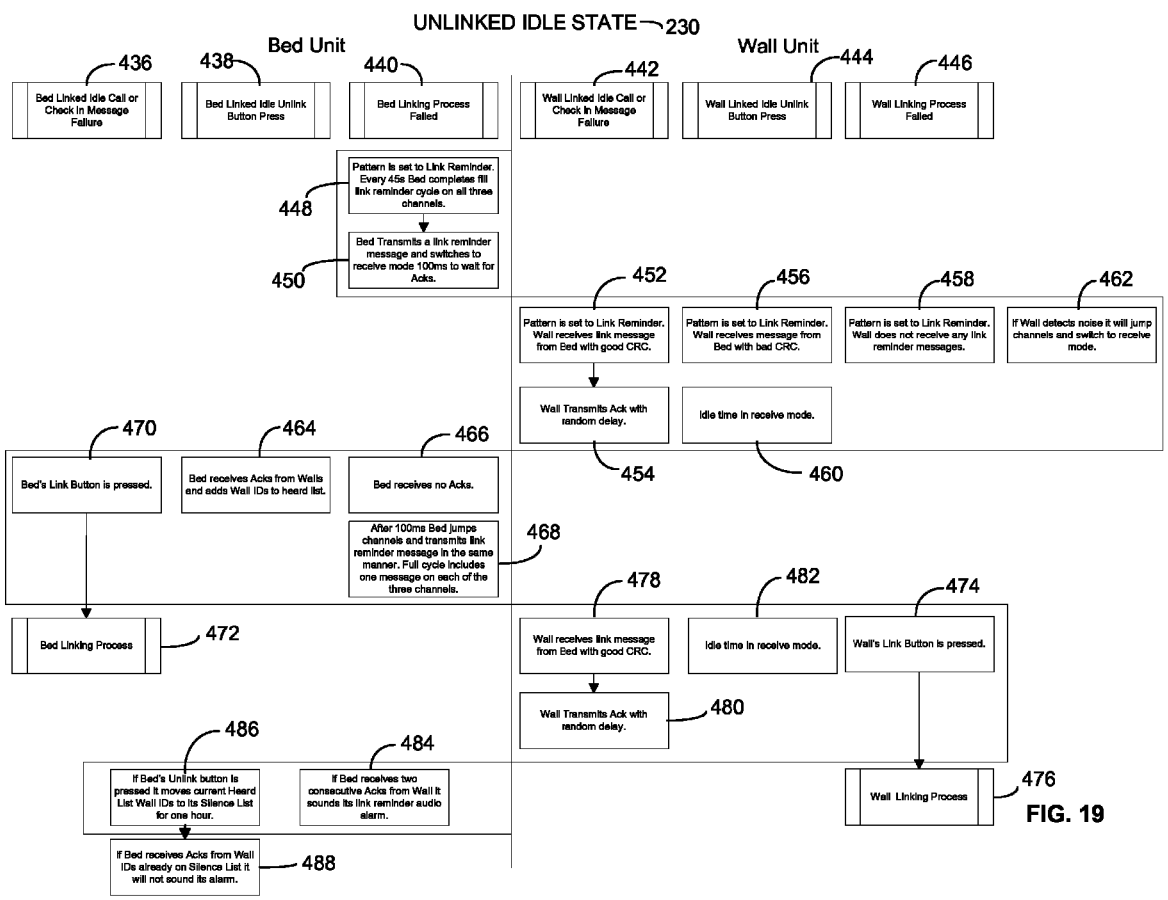
FIG. 19 is a flowchart illustrating the detailed operation of the Unlinked Idle State of FIG. 14.

Turning to FIG. 19, detailed operation of an embodiment of the unlinked idle state 230 is illustrated. The bed and wall units enter the unlinked idle state either due to failure of the communications link between a bed/wall unit pair, failure of the linking process, or when the health care provider activates the unlink button on one of the units, steps 436-446. While in the unlinked idle sleep mode, the bed unit completes periodic link reminder cycles, wherein it sends out a link reminder message on each of the operating channels and waits for acknowledgments from nearby unlinked wall units, steps 448, 450. Since an unlinked bed unit is not aware of the nearby wall unit's current operating channel, the bed unit repeats the link reminder cycle on each operating channel after a predetermined period. In embodiments, the bed unit repeats the link reminder cycle every 45 or 60 seconds. When the wall unit receives the link reminder message with correct CRC value, it responds with an Ack message, steps 452, 454. Alternatively, if the wall unit receives a link reminder message with a CRC error, or when the wall unit does not yet receive any link reminder messages, the wall unit remains in the idle receive mode, steps 456-460. While in the idle receive mode, the wall unit scans the current channel for noise and moves to another operating channel if it detects interference from nearby bed or wall units and/or other devices sharing its spectrum, step 462.

Upon receipt of the Ack messages from one or more nearby unlinked wall units, the bed unit logs each wall unit's unique identifier, which in this embodiment is the device serial number, in a list of wall IDs, step 464. If the bed unit is not in vicinity of an unlinked wall unit, it does not receive any Acks, step 466. After logging the wall IDs associated with the incoming Ack messages for 100 milliseconds, the bed unit moves to another channel to transmit the next link reminder message, step 468. If, in steps 470-476, the caregiver decides to activate the units' respective link buttons, both units transition to the linking process state 222. In steps 478, 480, the wall unit continues to respond with acknowledgement messages upon receipt of link reminders with correct CRC values. Otherwise, in step 482, the wall unit remains in the idle receive mode. When the bed unit receives two consecutive acknowledgments from the wall ID that is already on its wall ID list 464, the bed unit activates a link reminder alert to prompt the health care provider to initiate the linking process of the two nearby units, step 484. In this embodiment, the link reminder alert is an audio alarm, such as a short chirp. Other embodiments include using visual alerts, such as flashing one or more LEDs. If the health care provider wishes to deactivate the link reminder alert, the health care provider activates the bed unit's unlink button, which moves the list of wall IDs to a silence list for a predetermined duration, such as one hour, step 486. Consequently, the bed unit does not sound the link reminder alert if it subsequently receives acknowledgements from wall unit IDs already on the silent list, step 488.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method for maintaining a wireless communications link between a mobile unit gathering patient information and a stationary unit for processing the patient information, the method comprising:

repeatedly transmitting link status messages between the mobile and stationary units, each link status message occupying a nominal time slot and comprising one or more data fields for relaying the patient information between the mobile and stationary units and a collision indicator field for indicating a link status message collision;

providing an early indication of an onset of collisions of the link status messages transmitted by the mobile and stationary units with link status messages transmitted by another mobile and stationary unit pair by monitoring corruption of the collision indicator field, wherein the early indication of collisions comprises detecting the corruption of the collision indicator field prior to corruption of the data fields in the nominal time slot; and shifting subsequent transmissions of the link status messages when a collision is detected.

2. The method of claim 1 further comprising one of shifting a time reference of the subsequent transmissions of the link status messages and transmitting the link status messages on another operating channel when the collision is detected.

3. The method of claim 1 further comprising retrying the transmission of the link status messages on another operating channel when the wireless communications link is impaired due to a degradation in signal conditions.

4. The method of claim 1 further comprising routing the link status messages based on unique identifiers corresponding to each of the mobile and stationary units.

5. The method of claim 1 wherein the wireless communications link supports a message format for relaying the patient information to a hospital communications network and the link status messages include full frame transmissions according to the message format.

6. The method of claim 1 wherein the patient information includes at least one of a bed occupancy status signal, a nurse call signal, a nurse call assurance signal, a wireless communications link status signal, and an operating status signal associated with at least one of the units.

7. A method for maintaining wireless communications links, each link communicating patient information between a portable device attached to a portable hospital resource and a stationary device, the method comprising:
repeatedly transmitting link status messages over two or more of the wireless communications links, where the transmissions by each link are periodic;
providing an early indication of an onset of a collision between the two or more wireless communications links transmitting the link status messages, wherein the early indication of an onset of a collision comprises detecting a partial temporal overlap of the link status messages of the two or more wireless communications links prior to data corruption in the link status messages; and
shifting the repetition of the periodic link status messages in at least one of the wireless communications links when the collision is detected.

8. The method of claim 7 further comprising one of shifting a time reference of the repetition of the periodic link status messages and transmitting the link status messages on another operating channel when the collision is detected.

9. The method of claim 7 wherein the collision is detected by monitoring a collision indicator field in the link status messages.

10. The method of claim 7 further comprising retrying the transmission of the link status messages on another operating channel for at least one of the wireless communications links when the at least one wireless communications link is impaired due to a degradation in signal conditions.

11. The method of claim 7 wherein the wireless communications links support a message format for relaying the patient information to a hospital communications network and the link status messages include full frame transmissions according to the message format.

12. The method of claim 7 wherein the patient information includes at least one of an occupancy status signal associated with the portable hospital resource, a nurse call signal, a nurse call assurance signal, a wireless communications link status signal, and an operating status signal associated with at least one of the devices.

13. A system for maintaining a wireless communications link between a mobile hospital bed and a hospital communications network, the system comprising:
a first pair of transceivers supporting a wireless communications link between the mobile hospital bed and the hospital communications network;
one of the transceivers including an interface that enables the transceiver to function as a node of the hospital communications network; and
the other transceiver including circuitry for (1) repeatedly transmitting to the one transceiver link status messages, (2) providing an early indication of an onset of a collision of at least one of the link status messages with other communication links, wherein the early indication of the collision comprises detecting a partial temporal overlap of the link status messages of the first pair of transceivers with link status messages of a second pair of transceivers prior to data corruption in the link status messages of the first pair of transceivers, and (3) shifting transmissions of the link status messages in at least the first pair of transceivers subsequent to detection of the collision.

14. The system of claim 13 wherein the other transceiver further includes circuitry for one of shifting a time reference of the transmissions of the link status messages and transmitting the link status messages on another operating channel when the collision is detected.

15. The system of claim 13 wherein the collision is detected by monitoring a collision indicator field in the link status messages.

16. The system of claim 13 wherein the other transceiver further includes circuitry for retrying the transmission of the link status messages on another operating channel when the wireless communications link is impaired due to a degradation in signal conditions.

17. The system of claim 13 wherein the transceivers route the link status messages based on a unique identifier corresponding to each transceiver.

18. The system of claim 13 wherein the wireless communications link supports a message format for relaying the patient information to the hospital communications network and the link status messages include full frame transmissions according to the message format.

19. The system of claim 13 wherein the wireless communications link relays patient information to the hospital communications network, the patient information including at least one of a patient occupancy status signal associated with the mobile hospital bed, a nurse call signal, a call assurance signal, and a system status signal associated with at least one of the transceivers.

20. A mobile medical communications device for relaying patient information via a wireless communications link to a stationary site, the device comprising:
a transceiver for establishing a wireless communications link to the stationary site, where the wireless communications link supports a message format for relaying patient information to the stationary site;
a controller in communication with the transceiver and a source of patient information for (1) causing the transceiver to repeatedly transmit link status messages to the stationary site, thereby checking an integrity of the wireless communications link, and (2) shifting the repeatedly transmitted link status messages upon detection of a partial temporal overlap of the link status messages with link status messages associated with another mobile medical communications device and stationary site pair prior to data corruption in the link status messages of the mobile medical communications device; and a housing for the transceiver and the controller.

21. The mobile medical communications device of claim 20 wherein the controller causes the transceiver one of to shift a time reference of the transmissions of the link status messages and to transmit the link status messages on another operating channel when the collision is detected.

22. The mobile medical communications device of claim 20 wherein the partial temporal overlap is detected by monitoring a collision indicator field in the link status messages.

23. The mobile medical communications device of claim 20 wherein the controller causes the transceiver to retry the transmission of the link status messages on another operating channel when the wireless communications link is impaired due to a degradation in signal conditions.

24. The mobile medical communications device of claim 20 wherein the link status messages are routed between the mobile medical communications device and the stationary site based on their respective unique identifiers.

25. The mobile medical communications device of claim 20 wherein the link status messages include full frame transmissions according to the message format.

26. The mobile medical communications device of claim 20 wherein the patient information includes at least one of a patient occupancy status signal associated with the portable hospital resource, a nurse call signal, a call assurance signal, and a system status signal associated with at least one of the mobile medical communications device and the stationary site.

27. A stationary medical communications device for receiving patient information from a mobile telecommunications device attached to a portable hospital resource, the stationary medical communications device comprising:

a transceiver establishing a wireless communications link with the mobile telecommunications device; and a controller in communication with the transceiver for detecting corruption of one or more link status messages repeatedly transmitted by the mobile telecommunications device, and providing an indication that subsequent transmissions of the link status messages should be shifted to avoid future corruption, wherein the indication is associated with an early onset of a collision of the one or more link status messages due to a partial temporal overlap with link status messages associated with another mobile and stationary device pair prior to data corruption in the link status messages transmitted by the mobile telecommunications device.

28. The stationary medical communications device of claim 27 wherein in response to the indication the mobile telecommunications device changes one of a time reference and an operating channel of the subsequent transmissions of the link status messages.

29. The stationary medical communications device of claim 27 wherein the controller provides a further indication to retry the transmission of the link status messages on another operating channel when the wireless communications link is impaired due to a degradation in signal conditions.

30. The stationary medical communications device of claim 27 wherein the link status messages are routed between the stationary medical communications device and the mobile telecommunications device based on their respective unique identifiers.

31. The stationary medical communications device of claim 27 wherein the wireless communications link supports a message format for relaying the patient information to a hospital communications network and the link status messages include full frame transmissions according to the message format.

32. The stationary medical communications device of claim 27 wherein the patient information includes at least one of a patient occupancy status signal associated with the portable hospital resource, a nurse call signal, a call assurance signal, and a system status signal associated with at least one of the mobile telecommunications device and the stationary medical communications device.

33. The method of claim 7 wherein the partial temporal overlap is indicated by corruption of a collision indicator field of the link status messages when data fields of the link status messages remain uncorrupted subsequent to the collision.

34. The system of claim 13 wherein the partial temporal overlap is indicated by corruption of a collision indicator field of the link status messages in the first pair of transceivers when data fields of the link status messages in the first pair of transceivers remain uncorrupted subsequent to the collision.

35. The mobile medical communications device of claim 20 wherein the partial temporal overlap is indicated by corruption of a collision indicator field of the link status messages when data fields of the link status messages transmitted by the transceiver remain uncorrupted subsequent to a collision due to the partial temporal overlap.

36. The stationary medical communications device of claim 27 wherein the partial temporal overlap is indicated by corruption of a collision indicator field of the link status messages when data fields of the link status messages transmitted by the mobile telecommunications device remain uncorrupted subsequent to the collision.

* * * * *